(12) United States Patent
Yun et al.

(10) Patent No.: US 8,871,423 B2
(45) Date of Patent: Oct. 28, 2014

(54) PHOTORESIST COMPOSITION FOR FABRICATING PROBE ARRAY, METHOD OF FABRICATING PROBE ARRAY USING THE PHOTORESIST COMPOSITION, COMPOSITION FOR PHOTOSENSITIVE TYPE DEVELOPED BOTTOM ANTI-REFLECTIVE COATING, FABRICATING METHOD OF PATTERNS USING THE SAME AND FABRICATING METHOD OF SEMICONDUCTOR DEVICE USING THE SAME

(75) Inventors: Hyo-Jin Yun, Suwon-si (KR); Jae-Ho Kim, Yongin-si (KR); Young-Ho Kim, Yongin-si (KR); Boo-Deuk Kim, Suwon-si (KR); Jin-A Ryu, Hwaseong-si (KR); Myung-Sun Kim, Seoul (KR); Se-Kyung Baek, Hwaseong-si (KR); Soo-Kyung Kim, Suwon-si (KR); Ji-Yun Ham, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 401 days.

(21) Appl. No.: 13/015,869

(22) Filed: Jan. 28, 2011

(65) Prior Publication Data

US 2011/0189608 A1    Aug. 4, 2011

(30) Foreign Application Priority Data

Jan. 29, 2010   (KR) .......................... 10-2010-0008495
Jun. 11, 2010   (KR) .......................... 10-2010-0055662

(51) Int. Cl.
| | | |
|---|---|---|
| G03F 7/004 | (2006.01) | |
| G03F 7/38 | (2006.01) | |
| C07C 303/32 | (2006.01) | |
| C07C 309/06 | (2006.01) | |
| C07C 309/12 | (2006.01) | |
| G03F 7/039 | (2006.01) | |
| G03F 7/20 | (2006.01) | |

(52) U.S. Cl.
CPC .............. *G03F 7/004* (2013.01); *C07C 303/32* (2013.01); *G03F 7/0045* (2013.01); *C07C 309/12* (2013.01); *G03F 7/0397* (2013.01); *G03F 7/20* (2013.01); *C07C 309/06* (2013.01); *Y10S 430/122* (2013.01); *Y10S 430/123* (2013.01)
USPC ........ 430/270.1; 430/921; 430/922; 562/109; 562/113

(58) Field of Classification Search
CPC ... G03F 7/0397; G03F 7/0045; C07C 303/32; C07C 309/06; C07C 309/12
USPC .............. 430/191, 192, 193, 270.1, 921, 922; 562/109, 113
See application file for complete search history.

(56) References Cited

U.S. PATENT DOCUMENTS

| | | | |
|---|---|---|---|
| 5,624,787 A | | 4/1997 | Watanabe et al. |
| 5,976,770 A | * | 11/1999 | Sinta et al. ..................... 430/325 |
| 5,981,135 A | * | 11/1999 | Koes et al. ..................... 430/165 |
| 6,074,800 A | | 6/2000 | Breyta et al. |
| 6,706,461 B1 | * | 3/2004 | Sinta et al. ................. 430/270.1 |
| 7,399,577 B2 | * | 7/2008 | Yamato et al. ................ 430/311 |
| 7,455,948 B2 | * | 11/2008 | Taniguchi et al. ............ 430/176 |
| 7,491,484 B2 | * | 2/2009 | Yun et al. .................... 430/270.1 |
| 7,507,518 B2 | * | 3/2009 | Fujita et al. .................... 430/157 |
| 7,527,913 B2 | * | 5/2009 | Yun et al. .................... 430/270.1 |
| 2005/0164258 A1 | | 7/2005 | Goldberg et al. |
| 2008/0160448 A1 | * | 7/2008 | Yun et al. .................... 430/281.1 |
| 2008/0182203 A1 | * | 7/2008 | Yun et al. .................... 430/281.1 |
| 2009/0042114 A1 | * | 2/2009 | Yamato et al. ..................... 430/7 |
| 2009/0208872 A1 | * | 8/2009 | Wolf et al. ................. 430/286.1 |

FOREIGN PATENT DOCUMENTS

| | | |
|---|---|---|
| JP | 11-162846 | 6/1999 |
| JP | 2001-187780 | 7/2001 |
| KR | 1020040019611 A | 3/2004 |
| KR | 100703007 B1 | 3/2007 |

* cited by examiner

*Primary Examiner* — John Chu
(74) *Attorney, Agent, or Firm* — Myers Bigel Sibley & Sajovec, P.A.

(57) ABSTRACT

A photoresist composition for fabricating a probe array is provided. The photoresist composition includes a photoacid generator having an onium salt and an i-line reactive sensitizer.

13 Claims, 10 Drawing Sheets

PHOTORESIST COMPOSITION FOR FABRICATING PROBE ARRAY, METHOD OF FABRICATING PROBE ARRAY USING THE PHOTORESIST COMPOSITION, COMPOSITION FOR PHOTOSENSITIVE TYPE DEVELOPED BOTTOM ANTI-REFLECTIVE COATING, FABRICATING METHOD OF PATTERNS USING THE SAME AND FABRICATING METHOD OF SEMICONDUCTOR DEVICE USING THE SAME

CROSS-REFERENCE TO RELATED APPLICATION

This application claims priority from Korean Patent Applications No. 10-2010-0008495 filed on Jan. 29, 2010 and No. 10-2010-0055662 filed on Jun. 11, 2010 in the Korean Intellectual Property Office, and all the benefits accruing there from under 35 U.S.C. §119. The contents of which in their entireties are herein incorporated by reference.

FIELD OF THE INVENTION

The present invention relates to a photoresist composition for fabricating a probe array, a method of fabricating a probe array using the photoresist composition, a composition for photosensitive type developed bottom anti-reflective coating, a fabricating method of patterns using the same, and a fabricating method of a semiconductor device using the same. More particularly, the present invention relates to a photoresist composition for fabricating a probe array, which can be applied to i-line light, a method of fabricating a probe array using the photoresist composition, a composition for photosensitive type developed bottom anti-reflective coating, a fabricating method of patterns using the same, and a fabricating method of a semiconductor device using the same.

BACKGROUND

In recent years, with the advances of the genome project, genome nucleotide sequences of a variety of organisms have been found, which has increased interest in using probe arrays of biopolymer microchips. The probe array is extensively used to perform gene expression profiling and genotyping to detect mutation and polymorphism, such as single nucleotide polymorphism (SNP), to analyze proteins and peptides, to perform screening of potential drugs and to develop and fabricate new drugs.

Currently, a widely available probe array may be manufactured by, for example, exposing to light predetermined regions of a substrate which contain functional groups protected by a protective group, exposing the functional groups in the predetermined regions, and then performing in-situ synthesis of monomers.

Additionally, etching is of significance during semiconductor manufacture, and with the recent trend of high integration of semiconductor devices, a photolithography process is widely used in forming fine patterns of a semiconductor device.

In the photolithography process, a mask pattern, for example, a photoresist pattern, is formed, and a target mask to be etched is etched using the photoresist pattern as an etch mask. Here, in order to reduce light reflection of the target mask during exposure employed in the photolithography process, an anti-reflective coating may be employed.

In synthesizing probes of a probe array, in order to minimize damages of monomers, an i-line light source is generally used, and a non-ionic type photoacid generator is typically used as a photoacid generator for i-line light source. However, the non-ionic type photoacid generator generates a relatively weak acid. Thus, for the purpose of protecting a protective group that protects functional groups of the monomers, a light source of relatively high exposure energy should be used.

SUMMARY

The present invention provides a photoresist composition for fabricating a probe array, which deprotects a functional group with relatively low exposure energy.

The present invention also provides a method of fabricating a probe array using a photoresist composition for i-line light, which deprotects a functional group with relatively low exposure energy.

The present invention also provides a composition for photosensitive type developed bottom anti-reflective coating, which can form a to-be-etched film pattern having an improved profile.

The present invention also provides a fabricating method of a semiconductor device using a composition for photosensitive type developed bottom anti-reflective coating, which can form a to-be-etched film pattern having an improved profile.

These and other objects of the present invention will be described in or be apparent from the following description of some embodiments of the present invention.

According to an aspect of the present invention, there is provided a photoresist composition including a photoacid generator having an onium salt, and an i-line reactive sensitizer.

According to another aspect of the present invention, there is provided a method for fabricating a probe array including providing a substrate having a functional group capable of being coupled to a monomer immobilized on a surface thereof, the functional group protected by an acid-labile protective group, providing a photoresist composition on the substrate, the photoresist composition including a photoacid generator having an onium salt, and an i-line reactive sensitizer, selectively irradiating the photoresist composition using i-line light and deprotecting the functional group disposed on the selectively irradiated region, coupling the monomer to the deprotected functional group.

According to still another aspect of the present invention, there is provided a composition for a photosensitive type developed bottom anti-reflective coating, the composition including a photoacid generator having an onium salt, and an i-line reactive sensitizer.

According to a further aspect of the present invention, there is provided a method for forming patterns including forming a photosensitive type developed bottom anti-reflective coating by coating a composition for the photosensitive type developed bottom anti-reflective coating on a to-be-etched film, the composition comprising a first photoacid generator having an onium salt, and an i-line reactive sensitizer, forming a photoresist film on the photosensitive type developed bottom anti-reflective coating, simultaneously exposing the photoresist film and the photosensitive type developed bottom anti-reflective coating by irradiating i-line light, forming a photosensitive type developed bottom anti-reflective coating pattern and a photoresist pattern by developing the exposed photoresist film and the exposed photosensitive type developed bottom anti-reflective coating, and patterning the to-be-etched film using the photoresist pattern as an etch mask.

According to a further aspect of the present invention, there is provided a fabricating method of a semiconductor device including providing a substrate, forming a to-be-etched film on the substrate, forming a photosensitive type developed bottom anti-reflective coating by coating a composition for forming the photosensitive type developed bottom anti-reflective coating on the to-be-etched film, the composition comprising a first photoacid generator having an onium salt, and an i-line reactive sensitizer, forming a photoresist film on the photosensitive type developed bottom anti-reflective coating, simultaneously exposing the photoresist film and the photosensitive type developed bottom anti-reflective coating by irradiating i-line light, forming a photosensitive type developed bottom anti-reflective coating pattern and a photoresist pattern by developing the exposed photoresist film and the exposed photosensitive type developed bottom anti-reflective coating, and patterning the to-be-etched film using the photoresist pattern as an etch mask.

BRIEF DESCRIPTION OF THE DRAWINGS

The above and other features and advantages of the present invention will become more apparent by describing in detail embodiments thereof with reference to the attached drawings in which.

DETAILED DESCRIPTION OF THE EMBODIMENTS

Figure 1:
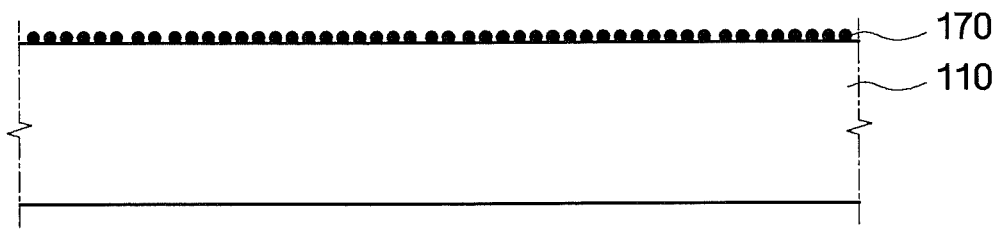
FIGS. 1 through 7 are cross-sectional views of intermediate products for explaining a method for fabricating a probe array according to an embodiment of the present invention.

Advantages and features of the present invention and methods of accomplishing the same may be understood more readily by reference to the following detailed description of embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the present invention will only be defined by the appended claims. Therefore, in some embodiments, well-known process procedures, structures, and techniques will not be described in detail to avoid misinterpretation of the present invention.

It will be understood that when an element or layer is referred to as being "coupled to," or "connected to" another element or layer, it can be directly coupled or connected to the other element or layer or intervening elements or layers may be present. In contrast, when an element is referred to as being "directly coupled to" or "directly connected to" another element or layer, there are no intervening elements or layers present. Like numbers refer to like elements throughout. As used herein, the term "and/or" includes any and all combinations of one or more of the associated listed items.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present invention.

The terminology used herein is for the purpose of describing particular embodiments only and is not intended to be limiting of the invention. As used herein, the singular forms are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

First, a photoresist composition for fabricating probe arrays according to embodiments of the present invention and a method of fabricating a probe array using the photoresist composition will be described in detail with reference to the accompanying drawings.

The photoresist composition for fabricating probe arrays according to embodiments of the present invention includes a photoacid generator having an onium salt and an i-line reactive sensitizer.

The onium salt of the photoacid generator includes a sulfonium salt, including a sulfonium salt cation portion represented by the formula (1) and a sulfonium salt anion portion represented by the formula (2):

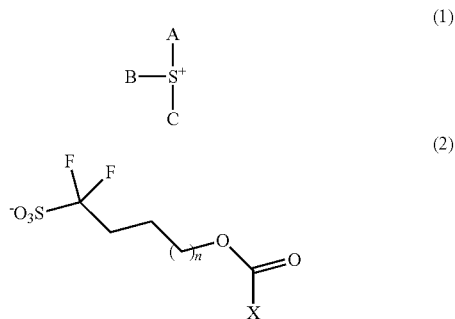

wherein in the formula (1), each of A, B, and C is one of a hydroxyl group, a cyclo group and a cycloalkyl group, and in the formula (2), n is an integer from 1 to 3, and X includes a C3-C10 cyclo group, an adamantyl group, or a cyclo heptane group containing oxygen.

In some embodiments, the sulfonium salt of the photoacid generator is represented by the formula (3):

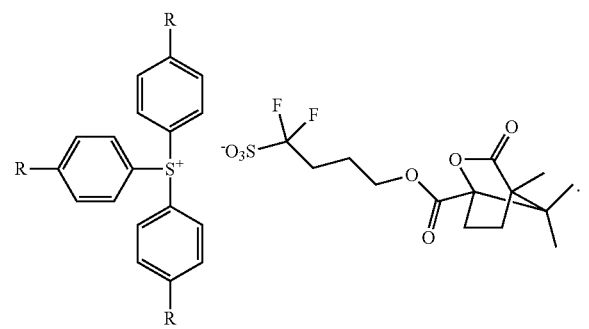

(3)

The photoacid generator represented by the formula (3) reacts with light to then generate a photoacid generator represented by the formula (4):

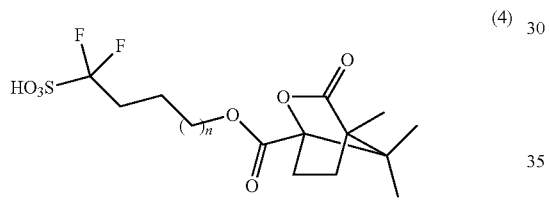

(4)

wherein n is 1.

Here, the reacting of the photoacid generator represented by the formula (3) with light may include activating the photoacid generator by a sensitizer absorbing i-line light to generate an acid. The sensitizer reacts with i-line light. Specifically, the sensitizer of the present invention absorbs i-line light and activates an acid generating reaction of the photoacid generator. That is to say, since the photoresist for fabricating the probe array according to embodiments of the present invention includes the i-line reactive sensitizer, in view of chormophore characteristics, the photoacid generator having an onium salt that is not reactive with i-line light is activated by the sensitizer absorbing the i-line light to start an acid generating reaction.

In an exemplary example, the sensitizer may include at least one of 2,4-isopropyl thioxanthone (ITX), benzophenone (BP), and butylbenzylphthalate (BBP) represented by the formulas (5-1) to (5-3), respectively:

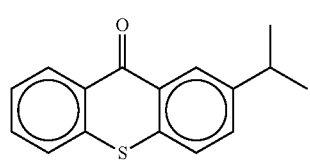

(5-1)

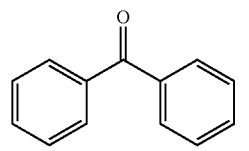

(5-2)

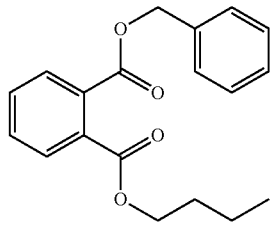

(5-3)

wherein i-line light refers to light having a wavelength of approximately 365 nm.

The photoresist composition for fabricating the probe array according to the present invention may further include a resin.

Here, the resin may include repeating units of a methacrylate monomer having a blocking group. In an exemplary example, the resin according to embodiments of the present invention may include methacrylate repeating units including blocking groups represented by the formulas (6-1) to (6-3):

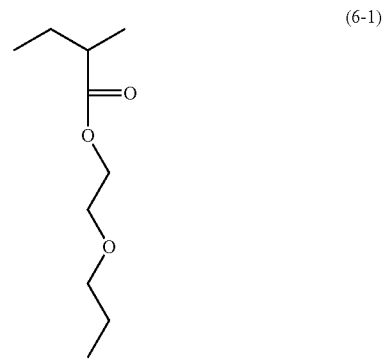

(6-1)

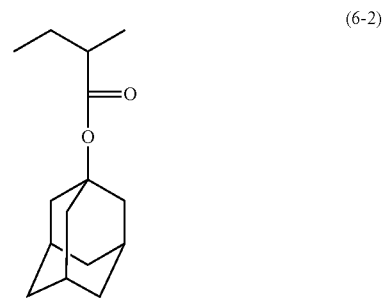

(6-2)

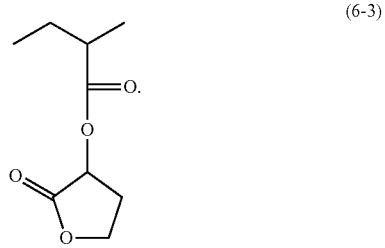

(6-3)

The photoresist composition for fabricating the probe array according to the present invention may include, for example, approximately 1 to 20 wt % of a resin, approximately 1 to 10 wt % of a photoacid generator, approximately 1 to 10 wt % of a sensitizer, and balance of a solvent. The balance of the solvent may include, for example, an organic solvent.

The photoresist composition for fabricating a probe array according to one embodiment of the present invention is capable of generating a relatively strong acid while being applied to an i-line light source, compared to a photoresist composition for fabricating a probe array including a non-ionic type photoacid generator, thereby deprotecting an acid-labile protective group with a small amount of light exposed.

Hereinafter, a method for fabricating a probe array according to an embodiment of the present invention will be described with reference to FIGS. 1 through 7. FIGS. 1 through 7 are cross-sectional views of intermediate products for explaining a method for fabricating a probe array according to an embodiment of the present invention.

Referring to FIG. 1, a substrate 110 having a functional group (180 of FIG. 3) on its surface, the functional group protected by an acid-labile protective group 170 and capable of coupling to a first monomer (161a of FIG. 4) of a probe.

The substrate 110 may be a flexible or rigid substrate. Usable examples of the flexible substrate may include a membrane or plastic film made of nylon or nitrocellulose. Usable examples of the rigid substrate may include a silicon substrate, a transparent glass substrate made of glass or quartz. Since the silicon substrate or the transparent glass substrate is transparent with respect to visible light and/or ultraviolet (UV) light, it can be advantageously used for detection using a marker. The silicon substrate or the transparent glass substrate is advantageous in that it can be manufactured by a process of producing various thin films and a photolithography process which are typically applied to a process of producing semiconductor devices or a process of producing LCD panels.

A plurality of probe cell regions 120 to be coupled to probes (161 and 162 of FIG. 7) may be defined in the substrate 110. Although not shown, the substrate 110 may be formed as a separate pattern using a material that is stable even by a contact with a probe cell region without being hydrolyzed. For example, the probe cell regions 120 may be made of a silicon oxide layer (such as a plasma enhanced-TEOS (PE-TEOS) layer, a high density plasma (HDP) oxide layer, a P—SiH$_4$ oxide layer, or a thermal oxide layer), a silicate such as hafnium silicate or zirconium silicate, a silicon nitride layer, a silicon oxynitride layer, a metal oxynitride layer (such as a hafnium oxynitride layer or a zirconium oxynitride layer), a metal oxide layer (such as a titanium oxide layer, a tantalum oxide layer, an aluminum oxide layer, a hafnium oxide layer, a zirconium oxide layer or an indium tin oxide (ITO) layer), a polyimide, a polyamine, a metal (such as gold, silver, copper or palladium), or a polymer such as polystyrene, polyacrylate, or polyvinyl. Alternatively, the probe cell regions 120 may also be made of materials that are stably used in the process of producing the semiconductors or the LCDs.

The functional group 180 formed on the substrate 110 is protected by the acid-labile protective group 170. The acid-labile protective group 170 may be used when the probe array is synthesized using photolithography, for example. When the acid-labile protective group 170 is coupled to the surface of the substrate 110, for example, the functional group 180 formed on the surface of the substrate 110, the substrate 110 is said to be protected. The surface of the substrate 110 coupled to the acid-labile protective group 170 can be deprotected by an acid. Here, the term "deprotection" is used to mean the removal of the acid-labile protective group 170 from the surface of the substrate 110 to expose the functional group 180 to the surface of the substrate 110. A probe array having a desired sequence can be fabricated by repeatedly performing the protection and deprotection steps. Examples of the acid-labile protective group may include, but are not limited to, t-BOC (tert-butyoxycarbonyl), DMT (dimethoxytrityl), and so on.

Although not shown, in some other embodiments of the present invention, the substrate 110 may further include a linker coupled to the functional group 180 formed on each of the plurality of probe cell regions A1 and A2. The functional group 180 can be immobilized on the plurality of probe cell regions A1 and A2 using the liker. The linker may make the coupling of each of the plurality of probe cell regions A1 and A2 with probes 161 and 162, or provide a spatial margin for, for example, hybridization between the probes 161 and 162 and a target sample so as to free interaction therebetween. Therefore, a linker molecule may have a sufficient length of, for example, 6 to 50 atoms, so as to allow free interaction between the probes 161 and 162 and the target sample.

Figure 2:
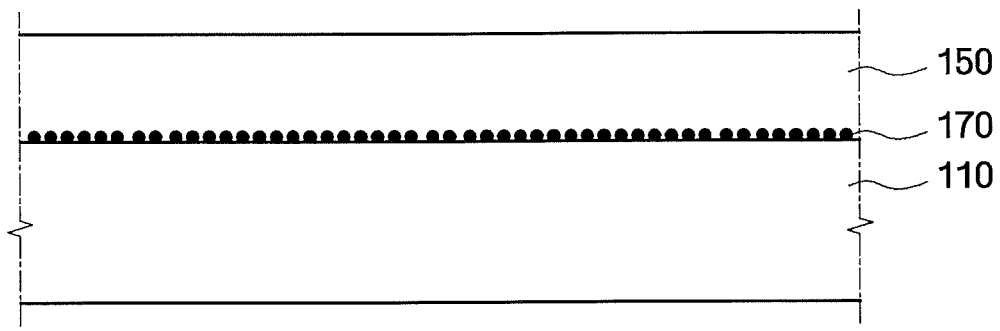

Next, as shown in FIG. 2, a photoresist 150 is provided on the substrate 110, the photoresist 150 including a photoacid generator having an onium salt, and an i-line reactive sensitizer.

As previously described, the onium salt of the photoacid generator includes a sulfonium salt, which includes a sulfonium salt cation portion represented by the formula (1) and a sulfonium salt anion portion represented by the formula (2):

(1)

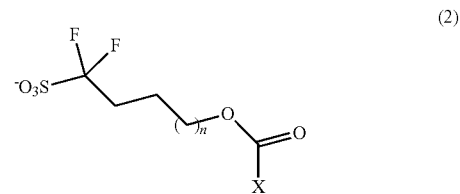

(2)

wherein in the formula (1), each of A, B, and C is one of a hydroxyl group, a cyclo group and a cycloalkyl group, and in the formula (2), n is an integer from 1 to 3, and X includes a C3-C10 cyclo group, an adamantyl group, or a cyclo heptane group containing oxygen.

In some embodiments, the sulfonium salt of the photoacid generator is represented by the formula (3), and the photoacid generator represented by the formula (3) reacts with light and generates a photoacid generator represented by the formula (4). Here, the reacting of the photoacid generator represented by the formula (3) with light means that the photoacid generator is activated by the sensitizer absorbing the i-line light to then generate an acid:

(3)

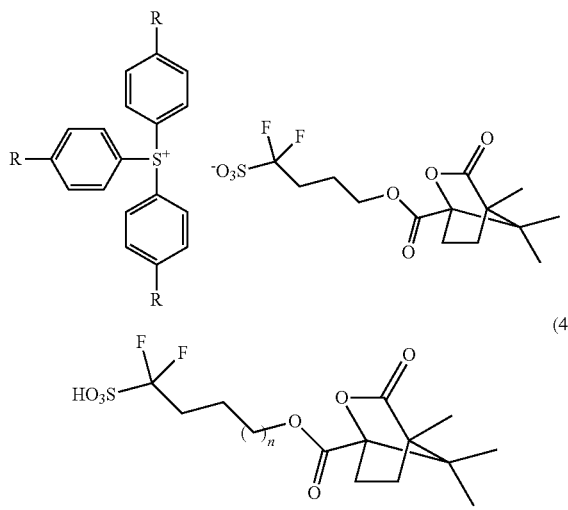

(4)

wherein n is 1.

Here, the sensitizer may include at least one of 2,4-isopropyl thioxanthone (ITX), benzophenone (BP), and butylbenzylphthalate (BBP) represented by the formulas (5-1) to (5-3), respectively:

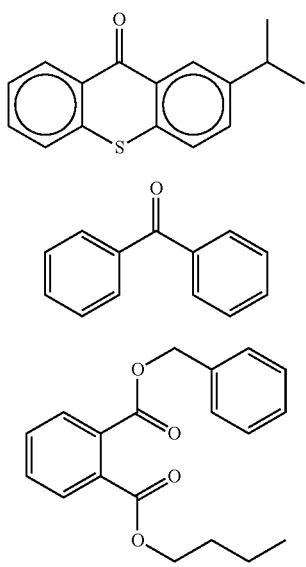

(5-1)

(5-2)

(5-3)

wherein i-line light refers to light having a wavelength of approximately 365 nm.

Further, the photoresist composition may further include a resin reacting with the acid generated by the photoacid generator, and detailed descriptions thereof are described above in the previous embodiment and will be not given herein.

The photoresist 150 may be provided on the substrate 110 by dispensing or spin coating.

Figure 3:
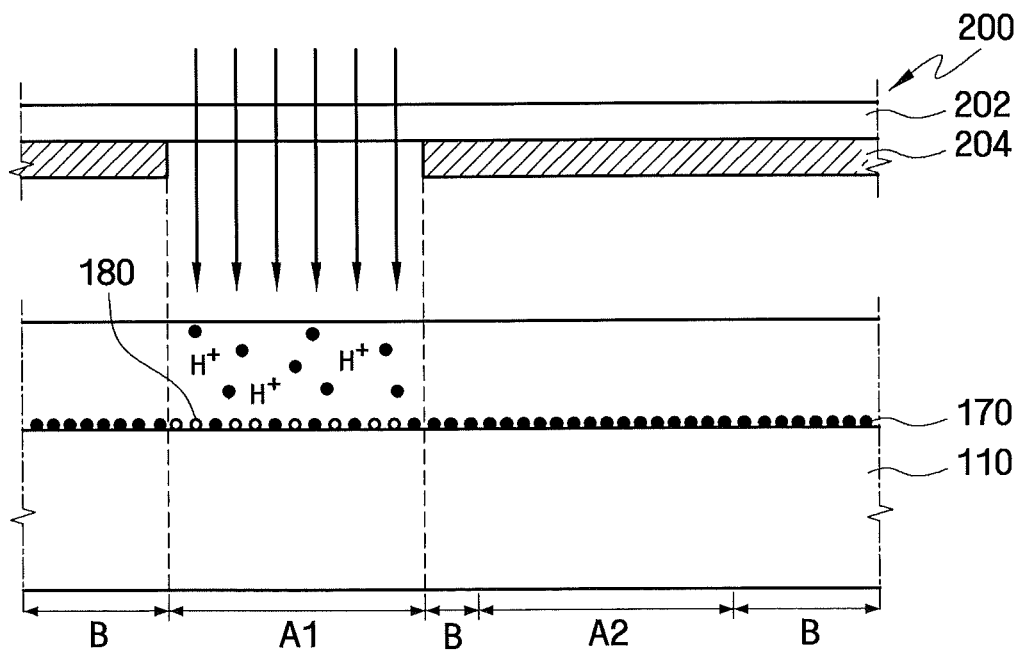

Next, referring to FIG. 3, i-line light is selectively irradiated into the photoresist 150, and the functional group 180 disposed in the region A1 that is selectively irradiated with i-line light is deprotected.

First, an optical mask 200 including a light-shielding pattern 204, for example, may be disposed on the substrate 110.

As shown, the optical mask 200 may include a transparent mask body 202 and a light-shielding pattern 204 formed on the mask body 202. That is to say, the light-shielding pattern 204 of the optical mask 200 may be defined as a light-shielding region, and a region other than the light-shielding pattern 204 may be defined as a light-transmitting region. In the selective exposure process of the photoresist 150, various types of optical masks, which are different from the shown optical mask 200, may be used. In some other embodiments, when the substrate 110 is a transparent substrate, the optical mask 200 may be disposed under the substrate 110. In some other embodiments, in a modified embodiment of the selective exposure using the optical mask 200, the photoresist 150 may be selectively exposed using an exposed group capable of performing selective exposure without using a separate optical mask.

When the optical mask 200 is aligned, an exposed region that is not shielded by the light-shielding pattern 204, that is, a light-transmitting region, may be disposed to corresponding to a region A1 which is capable of coupling with a probe or monomer.

More specifically, as shown, the substrate 110 may include a plurality of probe cell regions A1 and A2 where probes are to be formed, and a probe cell isolation region B where probes are not to be formed. The plurality of probe cell regions A1 and A2 may be separated from each other by the probe cell isolation region B. For example, as shown in FIG. 3, the surface of the substrate 110 in the probe cell isolation region B may be protected by the acid-labile protective group 170. That is to say, the surface of the substrate 110 corresponding to the probe cell isolation region B is not subjected to light irradiation due to the light-shielding pattern 204 of the optical mask 200, and the acid-labile protective group 170 may remain on the surface of the substrate 110 even by light irradiation.

In some other embodiments, the cell isolation region B of the substrate 110 are processed using various treatment methods to prevent monomers or probes from being coupled thereto. The probe cell isolation region B may be filled with a filler capable of blocking monomers or probes, for example, fluorides containing a fluorine group, or polysilicone. Alternatively, functional groups exposed to the surface of the substrate 110 are inactively capped using capping groups, thereby preventing monomers or probes from being coupled to the probe cell isolation region B.

In other words, the light-shielding pattern 204 of the optical mask 200 may be disposed to selectively expose a region corresponding to the probe cell region A1 for coupling with monomers, among the plurality of probe cell regions A1. For brevity of illustration, although two probe cell regions A1 and A2 are illustrated, three or more probe cell regions may also be used as the plurality of probe cell regions.

Next, the substrate 110 having the optical mask 200 is exposed to light. Here, i-line light is used.

As a result, the i-line light having passed through the exposed region A1 of the optical mask 200 reaches the photoresist 150 on the exposed region A1, so that the sensitizer in the photoresist 150 reacts with the i-line light. That is to say, the sensitizer absorbs the i-line light and activates an acid generating reaction of the photoacid generator. Included in the photoresist 150. Accordingly, the photoacid generator, activated by the sensitizer, generates an acid (H+), and the generated acid (H+) exists in the exposed region A1 to then deprotect the acid-labile protective group 170 coupled to the functional group. Thus, the functional group 180 capable of coupling with probes, oligomer probes or monomers is exposed. Here, the reactive functional group protected by the acid-labile protective group 170 may be, for example, a hydroxyl group, an amino group, or a sulfide group, but aspects of the present invention are not limited thereto.

When the photoresist 150 is selectively exposed, an exposure energy may be in a range of approximately 10 mJ to approximately 1000 mJ, specifically approximately 100 mJ. An acid generation extent of a photoacid generator having an onium salt is higher than a non-ionic type photoacid generator including another salt, thereby deprotecting the acid-labile protective group 170 with a relatively small exposure amount. Therefore, an exposure time can be considerably reduced by using the photoacid generator having an onium salt.

In addition, the sensitizer activates the onium salt type photoacid generator incapable of starting acid generation with i-line light to trigger the start of acid generation. Therefore, the i-line reactive sensitizer is used after being mixed with the photoacid generator having an onium salt, thereby stably deprotecting the acid-labile protective group 170 with a relatively small exposure amount even by using i-line light for preventing damages of monomers.

Figure 4:
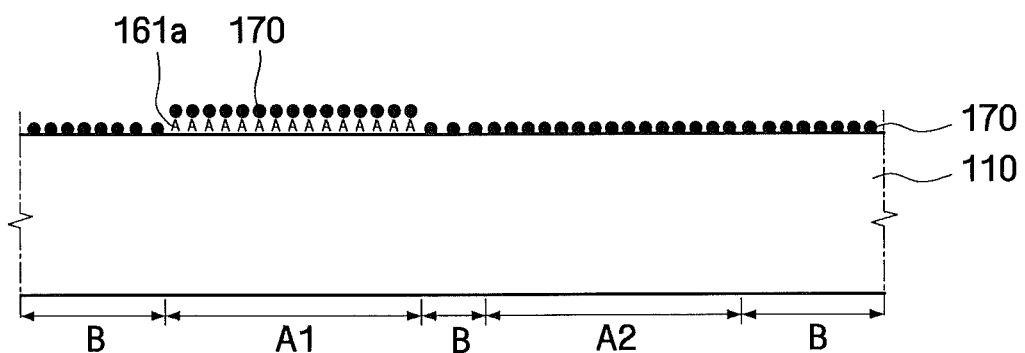

Referring to FIG. 4, the photoresist (150 of FIG. 2) is removed and a first monomer 161*a* coupled to the acid-labile protective group 170 is coupled to the deprotected functional group (180 of FIG. 3).

In-situ synthesis of an oligonucleotide probe will now be described by way of example. A nucleotide phosphoramidite monomer 161*a* having any one of bases adenine (A), guanine (G), thymine (T), cytosine (C), and uracil (U) may be coupled. FIG. 4 illustrates a case of nucleotide phosphoramidite monomer 161*a* having adenine (A) as a base. When it is necessary to additionally couple another monomer to the coupled monomer, the monomer provided for coupling may be the nucleotide phosphoramidite monomer 161*a* having adenine (A) as a base and the acid-labile protective group 170 combined therewith, which is referred to as a first monomer 161*a*.

As a result of the coupling, the first monomer 161*a* may be immobilized on a target probe cell active A1. Here, since the functional group 180 is not deprotected in a non-target probe cell active A2, unnecessary immobilization of monomers can be prevented. Therefore, it is possible to prevent immobilized probes from having a poor sequence or noises from being generated.

Although not shown, the functional group exposed during exposure but not coupled to the first monomer 161*a* may be inactively capped using, for example, a capping group. When the first monomer 161*a* is phosphoramidite, for example, phosphate trimester generated by a bond between phosphoramidite and a5'-hydroxy group is oxidized to convert the same into a phosphate structure. Here, usable examples of the inactive capping group may include acetic anhydride and/or N-methylimidazone. In addition, iodine (I) may be used during oxidation.

Figure 5:
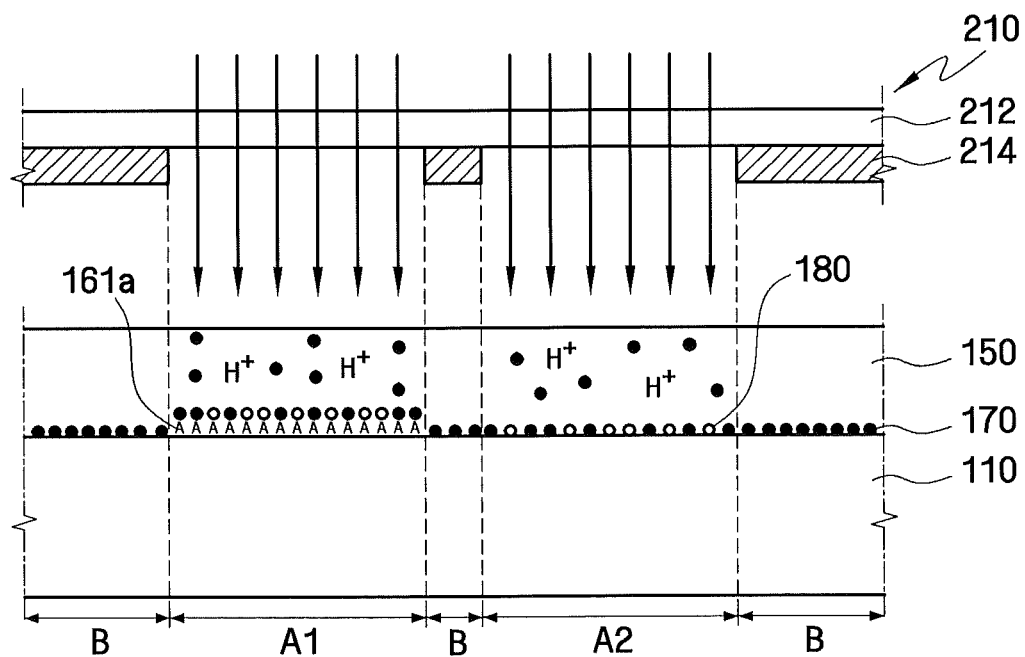

Referring to FIG. 5, the photoresist 150 including a photoacid generator having an onium salt, and an i-line reactive sensitizer is provided on the substrate 110 having the first monomer 161*a* coupled thereto, and the photoresist 150 is selectively exposed to deprotect the acid-labile protective group 170 corresponding to exposed regions A1 and A2, thereby exposing the functional group 180.

As previously described with reference to FIG. 3, second monomers (161*b* and 162*a* of FIG. 6), a body 212 of the optical mask 210 and a light-shielding pattern 214 may be disposed on the photoresist 150 including the photoacid generator and the sensitizer so as to correspond to to-be-coupled regions A1 and A2. Accordingly, acid (H+) is generated on the selectively exposed regions A1 and A2 of the photoresist 150 due to interaction between the sensitizer and the photoacid generator, and the acid-labile protective group 170 is deprotected by the generated acid (H+) and the functional group 180 is exposed.

Figure 6:
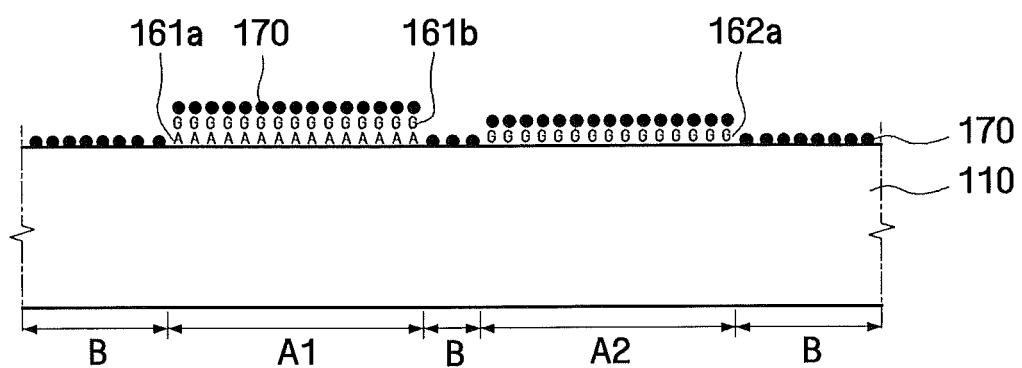

Referring to FIG. 6, the photoresist 150 is removed and the second monomers 161*b* and 162*a* coupled to the acid-labile protective group 170 are coupled to the deprotected functional group 180.

Figure 7:
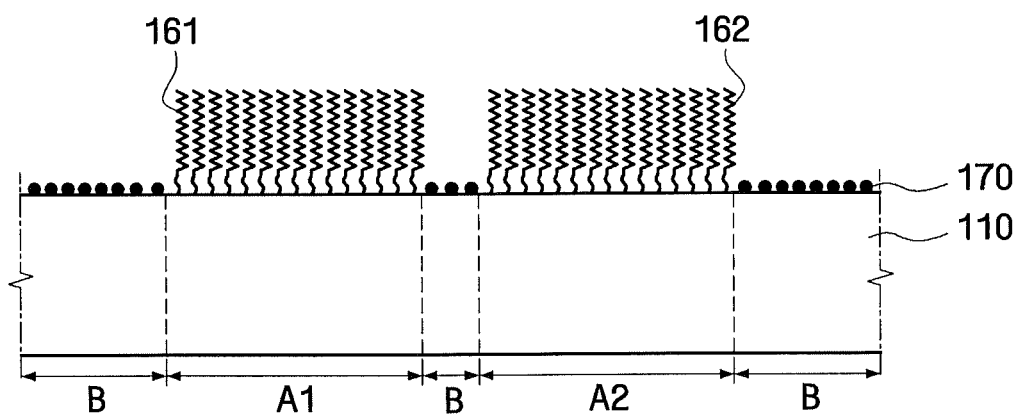

Next, as shown in FIG. 7, the selective deprotection and the coupling of monomers are repeatedly performed, thereby forming a plurality of probes coupled on the probe cell regions A1 and A2.

Accordingly, a plurality of probes 161 and 162 are formed on the plurality of probe cell regions A1 and A2 of the substrate 110, and the plurality of probe cell regions A1 and A2 may be physically, chemically separated from each other by the probe cell isolation region B.

The plurality of probes 161 and 162 immobilized on the plurality of probe cell regions A1 and A2 may be, for example, oligomer probes. Here, the oligomer may refer to a polymer formed of two or more covalently bonded monomers. The oligomer may include about 2 to about 500 monomers, and preferably about 5 to about 300 monomers. The oligomer may also include about 5 to about 100 monomers. Examples of the monomers include nucleosides, nucleotides, amino acids or peptides, according to the type of probe fixed to the oligomer probe array. Further, the monomers can include nucleosides, nucleotides, amino acids, peptides, etc., depending on the type of probes.

Nucleosides and nucleotides may include not only known purine and pyrimidine bases, but also methylated purines or pyrimidines, acylated purines or pyrimidines, etc.

Furthermore, nucleosides and nucleotides may include known ribose or deoxyribose saccharides, or include modified saccharides in which one or more hydroxyl groups are substituted by halogen atoms or aliphatics, or to which the functional group, such as ether or amine, is bonded.

Amino acids may include not only naturally occurring, L-, D-, and nonchiral amino acids, but also to unnatural amino acids, modified amino acids, amino acid analogs, etc.

Peptides generally refer to compounds produced by an amide bond between the carboxyl group of one amino acid and the amino group of another amino acid.

In the fabricating method of the probe array according to one embodiment of the present invention, the acid-labile protective group can be deprotected with a small amount of light exposed using i-line light, thereby considerably reducing an exposure time. Accordingly, the processing cost can be greatly reduced.

While the present invention has been particularly shown and described with reference to exemplary embodiments thereof, it will be understood by those of ordinary skill in the art that various changes in form and details may be made therein without departing from the spirit and scope of the present invention. Therefore, the examples are presented for illustrative purposes only and are not intended to restrict the scope of the invention.

Hereinafter, the present invention will be described in more detail by means of the following specific examples.

Specific experimental examples related to embodiments of the invention will now be described. Since descriptions not given in this specification can be sufficiently analogized by those skilled in the art, such descriptions will be omitted here.

EXPERIMENTAL EXAMPLE A 10 g of a solution was prepared by dissolving 0.5 g photoacid generators represented by the formula (7-1) and (7-2) in a mixed solution of tetrahydrofuran and water ($H_2O$) in a mixing ratio of 9:1. The pH of the prepared solution was measured before exposure, and the pH of the solution was measure after exposure to i-line light of 365 nm (Comparative Experimental Example 1 and Comparative Experimental Example 2).

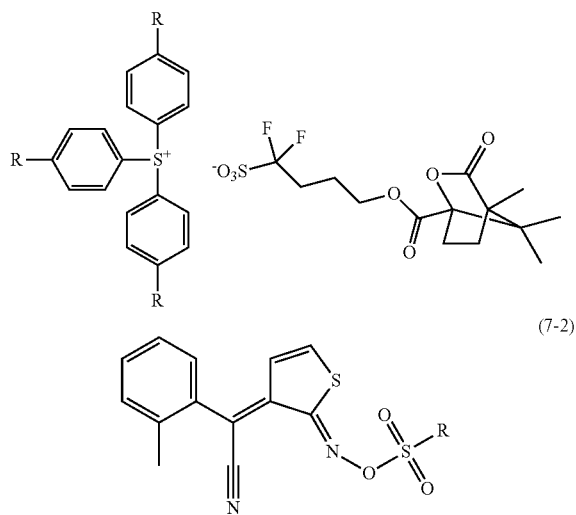

(7-1)

(7-2)

10 g of a solution was prepared by mixing the photoacid generator represented by the formula (7-1) and the sensitizer represented by the formula (7-3) in a mixing ratio of 1:1 by weight. The pH of the prepared solution was measured before exposure, and the pH of the solution was measure after exposure to i-line light of 365 nm (Experimental Example 1).

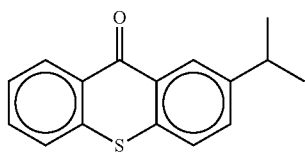

(7-3)

Measurement results of pH levels of the respective solutions with various exposure amounts are listed in Table 1.

TABLE 1

Measurement Results of pH levels depending on Exposure Energy

| | Time (sec) | | | | | | | |
|---|---|---|---|---|---|---|---|---|
| | 0 | 10 | 20 | 30 | 40 | 50 | 80 | 270 |
| Exposure Energy (mJ) | 0 | 135 | 270 | 405 | 540 | 675 | 1080 | 3645 |
| Comparative Experimental Example 1 (pH) | 6.25 | 6.95 | 6.87 | 6.75 | 6.69 | 6.44 | 6.01 | 4.5 |
| Comparative Experimental Example 2 (pH) | 5.39 | 5.07 | 5.06 | 5.12 | 5.11 | 5.14 | 5.14 | 5.1 |
| Experimental Example 1 (pH) | 4 | 3.91 | 3.77 | 3.68 | 3.63 | 3.62 | 3.38 | 2.51 |

Referring to Table 1, pH levels of Comparative Experimental Example 1 and Comparative Experimental Example 2 were higher than those of Experimental Example 1. That is to say, it is understood that acids were generated in the solutions with relatively small exposure amounts in Experimental Example 1. In more detail, when an exposure energy was 135 mJ, the solution of Experimental Example 1 had a pH level of 3.91 while the solutions of Comparative Experimental Example 1 and Comparative Experimental Example 2 had pH levels of 6.95 and 5.07, respectively. That is to say, the photoacid generator of Experimental Example 1, having an onium salt and an i-line reactive sensitizer, could generate an acid with a lower pH level with a smaller exposure energy than the photoacid generator of Comparative Experimental Example 1 having an onium salt and the non-ionic type photoacid generator of Comparative Experimental Example 2.

Further, when exposed with an exposure energy 3645 mJ, the pH level of the solution of Comparative Experimental Example 1 was 4.5, which is a pH level of an acid enough to deprotect the acid-labile protective group in the photoacid generator. However, since the exposure energy of 3645 mJ is so high as to cause damages to monomers, it cannot be appropriately used in fabricating probe arrays.

EXPERIMENTAL EXAMPLE B

DNA 1-Mer Stack

Preparation of Wafer

A wafer was cleaned using a piranha solution, and a surface of the wafer was silanized, followed by reacting in a spacer solution.

Preparation of First DNA Layer

The wafer was exposed with an exposure energy of 10 J and cleaned using acrylonitrile. An exposed portion of the wafer was reacted with DMT-dA and cleaned using acrylonitrile.

Coating and Exposure of Photoresist

The solutions prepared in Comparative Experimental Example 1, Comparative Experimental Example 2, and Experimental Example 1 of Experimental Example A, that is to say, the photoresists were coated on the wafers, respectively, and baked at 80° C. for 30 seconds. The wafer was exposed using i-line light of 365 nm. Here, the wafers coated with the photoresists prepared in Comparative Experimental Example 1, Comparative Experimental Example 2 and Experimental Example 1 were irradiated with exposure energies of 100 mJ and 500 mJ. The exposed wafers were subjected to post-exposure bake (PEB) treatment at 100° C. for 10 seconds and cleaned using acrylonitrile for removal of the photoresists, respectively.

Fluorescein Test

A solution of fluorescein amidite (F-amidite):DMT-dA: Activator 42™ mixed in a mixing ratio of 1:1.5:6.25 by volume (v/v) was prepared, and the prepared solution was reacted with the photoresist having the wafers removed. Subsequently, the resultant products were allowed to stand without disturbing at room temperature for 30 minutes, and the wafers were cleaned using acrylonitrile, followed by reacting with methanol. Next, the cleaned wafers were reacted with methanol in each beaker. Then, ethylenediamine was put into the beaker, and the same amount of ethanol was added. After completion of the reaction, the wafers were dried using a nitrogen ($N_2$) gas. Then, fluorescence intensity of each wafer was observed using a fluorescence scanner for a biochip.

Figure 8:
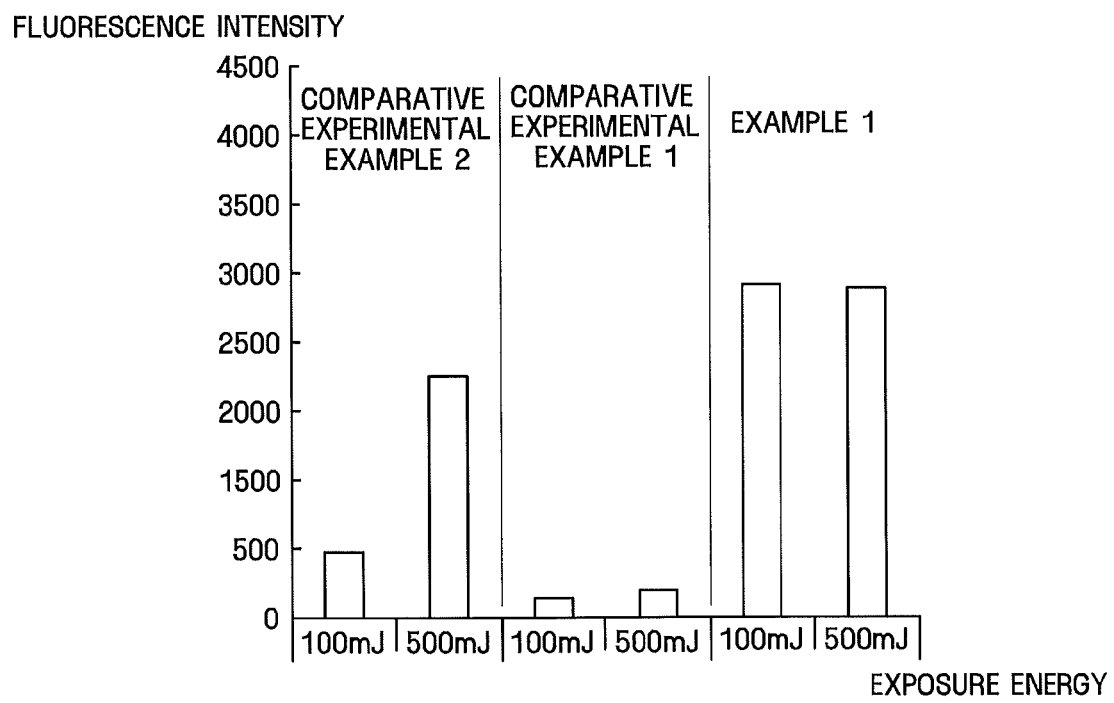
FIG. 8 is a graph illustrating a measurement result of fluorescence intensity for DNA 1-mer stack wafers according to Comparative Experimental Examples and Experimental Examples.

The fluorescence intensity of each of the photoresists prepared in Comparative Experimental Example 1, Comparative Experimental Example 2 and Experimental Example 1 of Experimental Example A was measured with exposure energies of 100 mJ and 500 mJ, and the measurement results are shown in FIG. 8.

As shown in FIG. 8, the photoresist prepared in Comparative Experimental Example 1, that is, the photoresist including only a photoacid generator having an onium salt, demonstated a low fluorescence intensity to i-line light with exposure energies of 100 mJ and 500 mJ. The photoresist prepared in Comparative Experimental Example 2, that is, the photoresist including only a non-ionic type photoacid generator, demonstated a relatively high fluorescence intensity to i-line light with an exposure energy of 500 mJ while demonstrating a low fluorescence intensity of 500 or less to i-line light with an exposure energy of 100 mJ.

However, the photoresist prepared in Experimental Example 1, that is, the photoresist including a photoacid generator having an onium salt and an i-line reactive sensitizer, demonstrated a relatively high fluorescence intensity to i-line light with exposure energies of 100 mJ and 500 mJ. Particularly, when a relatively low exposure energy of 100 mJ was employed, substantially the same level of fluorescence intensity was measured in the photoresist prepared in Experimental Example, compared to a case when a relatively high exposure energy of 500 mJ was employed. This confirms that use of the photoresist composition for fabricating the probe arrays according to embodiments of the present invention provided effective deprotection of acid-labile protective groups with a relatively low exposure energy.

EXPERIMENTAL EXAMPLE C

Figure 9:
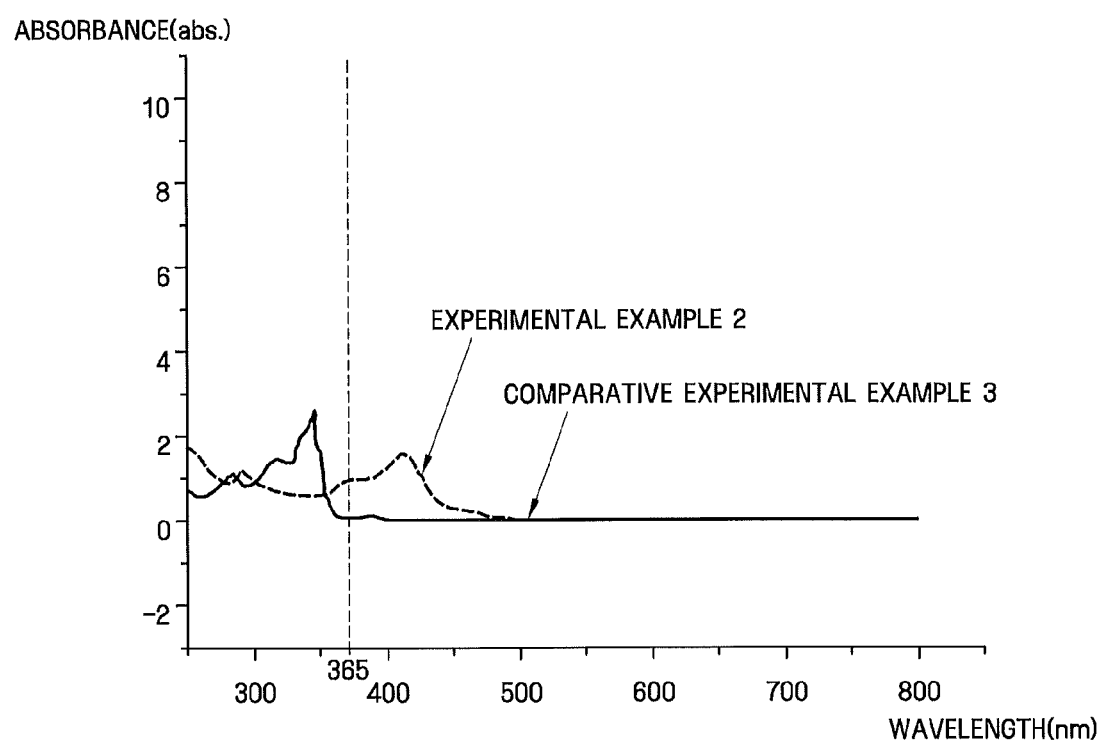
FIG. 9 is a graph illustrating a change in the absorbance depending on wavelengths of photoresists according to Comparative Experimental Example and Experimental Example.

FIG. 9 is a graph illustrating a change in the absorbance depending on wavelengths of a photoresist including only a photoacid generator having an onium salt (Comparative Experimental Example 3) and a photoresist including a photoacid generator having an onium salt and an i-line reactive sensitizer (Experimental Example 2).

In the graph shown in FIG. 9, the horizontal axis indicates a change in the wavelength (nm) and the vertical axis indicates absorbance (abs.). As shown in FIG. 9, the photoresist including only a photoacid generator, prepared in Comparative Experimental Example 3, showed absorbance of approximately 0 to light having a wavelength of 365 nm. By contrast, the photoresist including a photoacid generator having an onium salt and an i-line reactive sensitizer, prepared in Experimental Example 2, showed absorbance of approximately 1 to light having a wavelength of 365 nm. That to say, it was confirmed that the photoresist of Experimental Example 2 had increased absorbance compared to the photoresist of Comparative Experimental Example 3.

Hereinafter, a composition for forming the photosensitive type developed bottom anti-reflective coating according to embodiments of the present invention, a method for forming patterns using the same, and a fabricating method of a semiconductor device using the same will be described in greater detail with reference to the accompanying drawings.

First, the composition for forming the photosensitive type developed bottom anti-reflective coating according to embodiments of the present invention will be described in detail.

The composition for forming the photosensitive type developed bottom anti-reflective coating according to one embodiment of the present invention includes a photoacid generator having an onium salt and an i-line reactive sensitizer.

The onium salt of the photoacid generator includes a sulfonium salt, which includes a sulfonium salt cation portion represented by the formula (1) and a sulfonium salt anion portion represented by the formula (2):

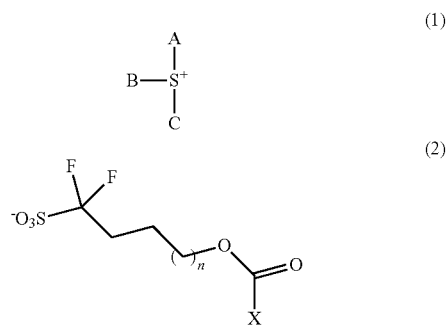

wherein in the formula (1), each of A, B, and C is one of a C1-C20 alkyl group, a C2-C20 alkoxy alkyl group, a C4-C20 aryl group, a C3-C20 cycloalkyl group, and a C5-C20 alkoxy cycloalkyl group, and in the formula (2), n is an integer from 1 to 3, and X includes a C4-C10 cyclo group, an alkyl group, a cycloalkyl group, an adamantyl group, or a cyclo heptane group containing oxygen.

In some embodiments, the sulfonium salt of the photoacid generator is represented by the formula (3):

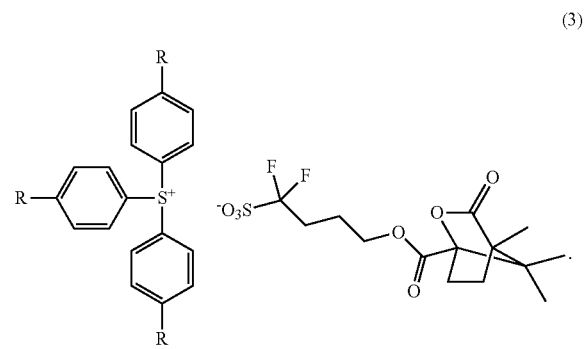

The photoacid generator represented by the formula (3) reacts with light to produce a photoacid generator represented by the formula (4), and the reaction of the photoacid generator represented by the formula (3) with light means that the photoacid generator is activated by the sensitizer absorbing the i-line light to then generate an acid:

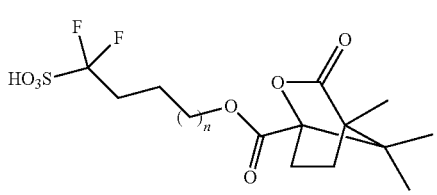
(4)

wherein n is 1.

The sensitizer reacts with i-line light. In more detail, the sensitizer of the present invention absorbs i-line light and activates an acid generating reaction by the photoacid generator. That is to say, since the photoresist for fabricating probe arrays according to embodiments of the present invention includes an i-line reactive sensitizer, in view of chromophore characteristics, the photoacid generator having an onium salt that is not reactive with i-line light is activated by the sensitizer absorbing the i-line light to start an acid generating reaction.

In an exemplary example, the sensitizer may include at least one of 2,4-isopropyl thioxanthone, benzophenone, and butyl benzyl phthalate, which are represented by the formulas (5-1) to (5-3), respectively:

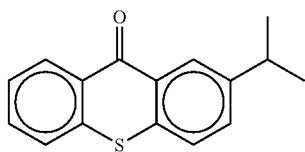
(5-1)

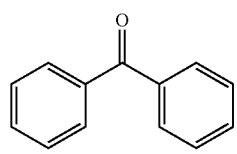
(5-2)

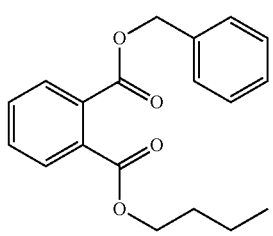
(5-3)

wherein the i-line light refers to light having a wavelength of approximately 365 nm.

Additionally, the composition for forming the photosensitive type developed bottom anti-reflective coating according to the present invention may further include a polymer resin represented by the formula (6):

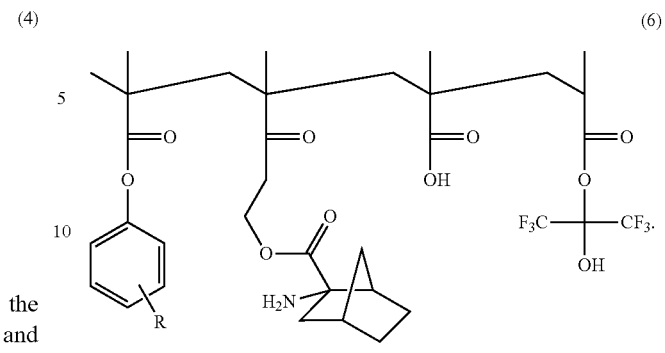
(6)

The composition for forming the photosensitive type developed bottom anti-reflective coating according to the present invention may further include a crosslinker.

The crosslinker is a material for crosslinking the polymer resin. In addition, the composition for forming the photosensitive type developed bottom anti-reflective coating according to an embodiment of the present invention may further include a thermal type crosslinker. Further, the composition for forming the photosensitive type developed bottom anti-reflective coating according to an embodiment of the present invention may further include a material represented by the formula (7):

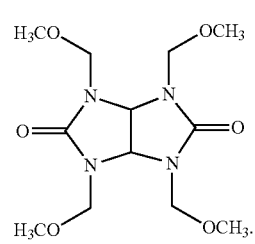
(7)

The composition for forming the photosensitive type developed bottom anti-reflective coating according to an embodiment of the present invention may include approximately 1 to approximately 40 wt % of the polymer resin, approximately 1 to approximately 10 wt % of the photoacid generator, approximately 1 to approximately 10 wt % of the sensitizer, approximately 5 to approximately 20 wt % of the crosslinker, and balance of a solvent. The balance of the solvent may include, for example, a mixed solvent of PGMEA/GBL.

In the composition for forming the photosensitive type developed bottom anti-reflective coating according to an embodiment of the present invention, with respect to i-line light, photosensitive type patterns, rather than thermal type patterns, are formed, thereby improving image contrast and allowing the formed patterns to have a better profile.

Hereinafter, a method for forming patterns using compositions for photosensitive type anti-reflective coatings according to the present invention will be described with reference to FIGS. 10 through 14. FIGS. 10 through 14 are cross-sectional views for explaining a method for forming patterns using compositions for photosensitive type anti-reflective coatings according to embodiments of the present invention.

Figure 10:
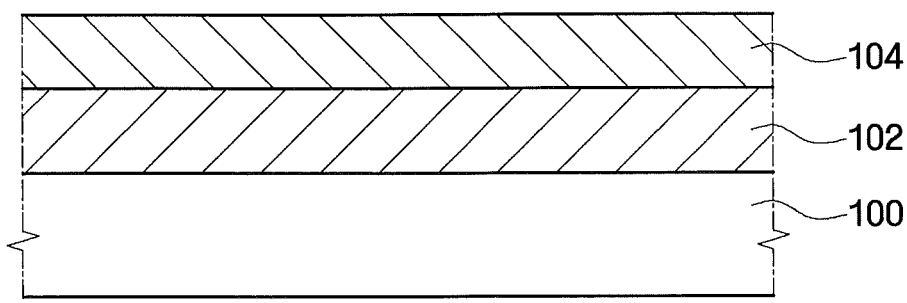
FIGS. 10 through 14 are cross-sectional views for explaining a method for forming patterns using compositions for photosensitive type anti-reflective coatings according to embodiments of the present invention.

Referring to FIG. 10, a composition for forming a photosensitive type developed bottom anti-reflective coating is coated on a to-be-etched film 1020, the composition including a first photoacid generator having an onium salt and an i-line light reactive sensitizer, thereby forming a photosensitive type developed bottom anti-reflective coating 1040.

The to-be-etched film 1020 may be, for example, a material layer formed on a semiconductor substrate 1000. Examples of the material layer may include, but are not limited to, a silicon nitride film, a polysilicon film, a silicon oxide film and other films. Further, although not shown in the drawing, a surface of the to-be-etched film 1020 may be cleaned in order to remove contaminants remaining on the to-be-etched film 1020.

The photosensitive type developed bottom anti-reflective coating 1040 may include a composition for forming a photosensitive type developed bottom anti-reflective coating, the composition including a first photoacid generator having an onium salt and an i-line reactive sensitizer. Details of the composition for forming a photosensitive type developed bottom anti-reflective coating used in the embodiments of the present invention are substantially the same as described above.

Next, after the photosensitive type developed bottom anti-reflective coating 1040 is formed, it is subjected to drying and bake processes to cause cross linking to the photosensitive type developed bottom anti-reflective coating 1040. In an exemplary embodiment, the bake process may be performed at a temperature in a range of approximately 150 to approximately 210° C. for approximately 50 seconds.

Figure 11:
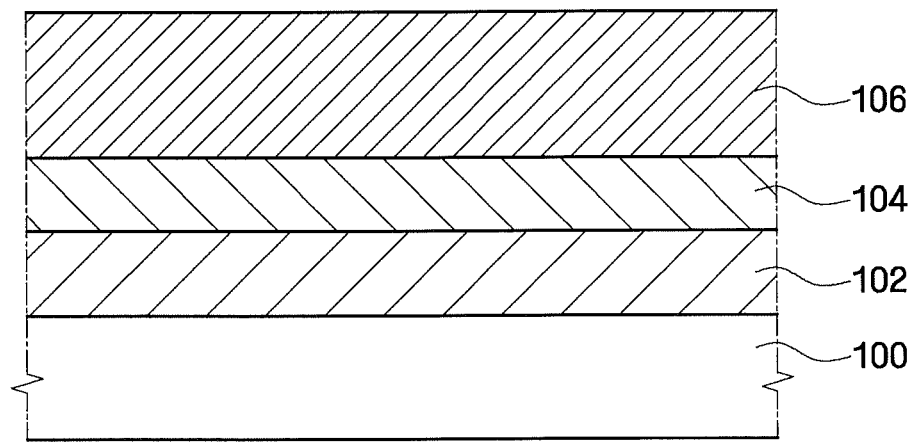

Referring to FIG. 11, a photoresist film 1060 is formed on the photosensitive type developed bottom anti-reflective coating 1040.

In more detail, a photoresist is coated on the photosensitive type developed bottom anti-reflective coating 1040 to form the photoresist film 1060. Here, the photoacid generator included in the photoresist film 1060 may be a different material from the photoacid generator included in the photosensitive type developed bottom anti-reflective coating 1040. In some other embodiments, the same photoacid generator may be used in forming the photoresist film 1060.

Further, the substrate 1000 having the photoresist film 1060 is subjected to a soft bake process. In an exemplary embodiment, the soft bake process may be performed at a temperature in a range of approximately 100 to approximately 160° C. for approximately 50 seconds.

Figure 12:
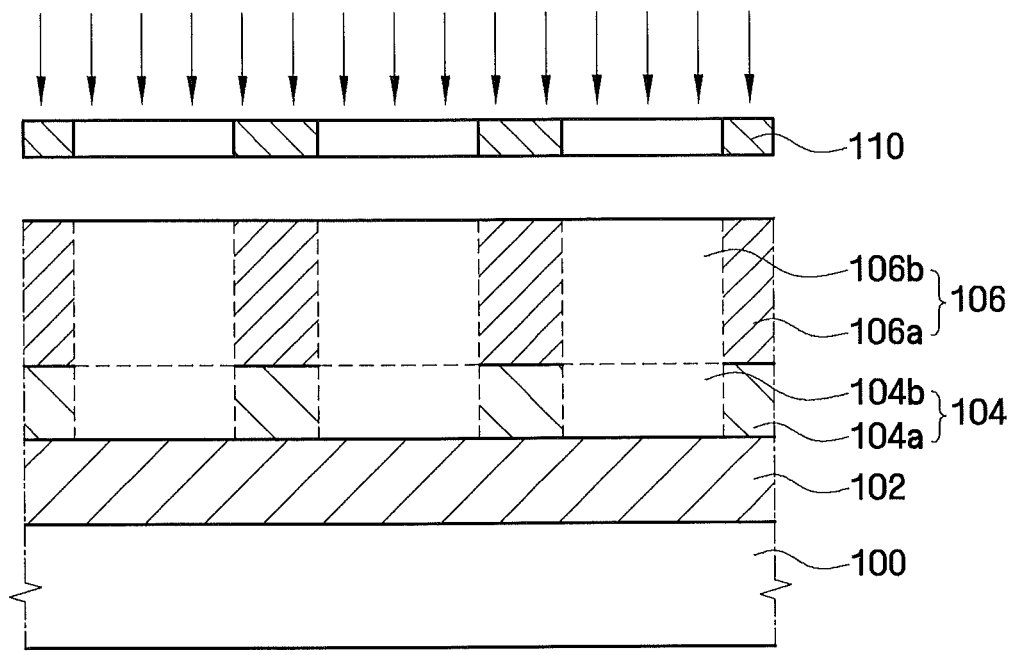

Referring to FIG. 12, the photoresist film 1060 and the photosensitive type developed bottom anti-reflective coating 1040 are simultaneously exposed by irradiating i-line light.

More specifically, an exposure mask 1100 may be disposed on the photoresist film 1060 using an exposure apparatus. The exposure mask 1100 has a predetermined pattern. The i-line light is irradiated onto the exposure mask 1100, so that a predetermined portion of the photoresist film 1060 formed on the substrate 1000 may selectively react with the i-line light having transmitted the exposure mask 1100. Here, the i-line light may be, for example, light having a wavelength of approximately 365 nm. Further, as the result of the exposure process, the photosensitive type developed bottom anti-reflective coating 1040 existing under the photoresist film 1060 may also be exposed to light.

For example, when the photoresist film 1060 is formed of a positive type photoresist, the photoresist film 1060*b* of the exposed region may be relatively hydrophilic, compared to the photoresist film 1060*a* of the non-exposed region. Accordingly, the photoresist film 1060*b* of the exposed region may have a solubility different from that of the photoresist film 1060*a* of the non-exposed region. In addition, the photosensitive type developed bottom anti-reflective coating 1040 may include an exposed region 1040*b* and a non-exposed region 1040*a*.

Next, a bake process is performed to allow predetermined patterns defined in the photoresist film 1060 and the photosensitive type developed bottom anti-reflective coating 1040 to be easily dissolved in a specific solvent. In an exemplary embodiment, the bake process may be performed at a temperature in a range of approximately 100 to approximately 160° C. for approximately 50 seconds.

In some embodiments, when the photoresist film 1060 and the photosensitive type developed bottom anti-reflective coating 1040 are both of a positive type, the exposed region resulting from the previous exposure process, that is, the photoresist film 1060*b* of the exposed region and the photosensitive type developed bottom anti-reflective coating 1040*b* of the exposed region, may be readily dissolved in a specific solvent. Conversely, when the photoresist film 1060 and the photosensitive type developed bottom anti-reflective coating 1040 are both of a negative type, the non-exposed region may be readily dissolved in a specific solvent. This is evident to those of ordinary skill in the related art. The invention will be described by way of example with regard to the positive-type photoresist film 1060 and the positive-type photosensitive type developed bottom anti-reflective coating 1040. Detailed descriptions of the negative-type photoresist film 1060 and the negative-type photosensitive type developed bottom anti-reflective coating 1040 will be omitted.

Figure 13:
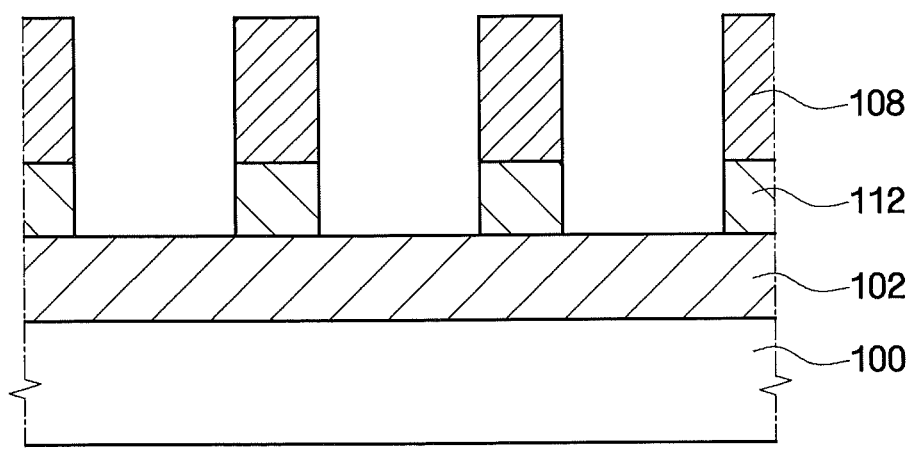

Referring to FIG. 13, the exposed photoresist film 1060*b* and the exposed photosensitive type developed bottom anti-reflective coating 1040*b* are developed to form the photosensitive type developed bottom anti-reflective coating pattern 1120 and the photoresist pattern 108.

More specifically, the exposed photoresist film 1060*b* and the exposed photosensitive type developed bottom anti-reflective coating 1040*b* are dissolved using a developer solution and then removed, thereby forming the photoresist pattern 108 and the photosensitive type developed bottom anti-reflective coating pattern 1120. In other words, the exposed photoresist film 1060*b* and the exposed photosensitive type developed bottom anti-reflective coating 1040*b* are sequentially dissolved and removed to then form the photoresist pattern 1080. Then, it is not necessary to perform a separate etching process for forming the anti-reflective coating pattern. Therefore, a loss of the photoresist pattern 1080 can be avoided.

Further, the use of the composition for forming the photosensitive type developed bottom anti-reflective coating according to embodiments of the present invention can improve image contrast, thereby forming a pattern having an improved profile.

Figure 14:
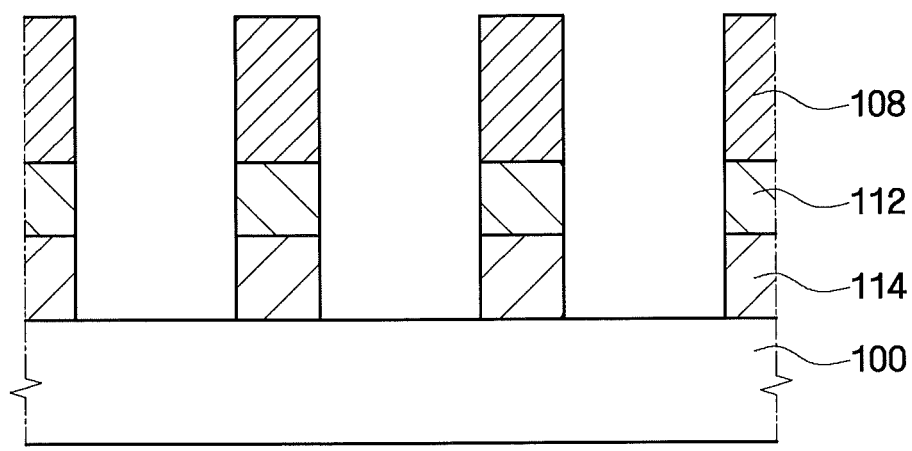

Next, referring to FIG. 14, the to-be-etched film 1120 is patterned using the photoresist pattern 1080 as an etch mask.

Hereinafter, a fabricating method of a semiconductor device using the photosensitive type developed bottom anti-reflective coating composition according to one embodiment of the present invention will be described.

The fabricating method of the semiconductor device may include providing a substrate; forming a to-be-etched film on the substrate; forming a photosensitive type developed bottom anti-reflective coating by coating a composition for forming the photosensitive type developed bottom anti-reflective coating on the to-be-etched film, the composition comprising a first photoacid generator having an onium salt, and an i-line reactive sensitizer; forming a photoresist film on the photosensitive type developed bottom anti-reflective coating; simultaneously exposing the photoresist film and the photosensitive type developed bottom anti-reflective coating by irradiating i-line light; forming a photosensitive type developed bottom anti-reflective coating pattern and a photoresist pattern by developing the exposed photoresist film and the exposed photosensitive type developed bottom anti-reflective coating; and patterning the to-be-etched film using the photoresist pattern as an etch mask.

The fabricating method of the semiconductor device is substantially the same as or similar to the method for forming the composition using the photosensitive type developed bottom anti-reflective coating and the method for forming patterns using the same, and thus, a detailed description will be omitted.

EXPERIMENTAL EXAMPLE D

Figure 15A:
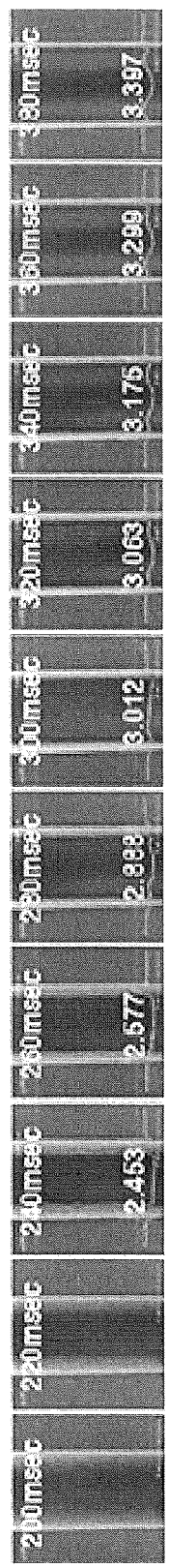
FIGS. 15A and 15B are SEM (Scanning Electron Microscope) photographs of patterns using a thermal type anti-reflective coating and a photosensitive type anti-reflective coating.
Figure 15B:
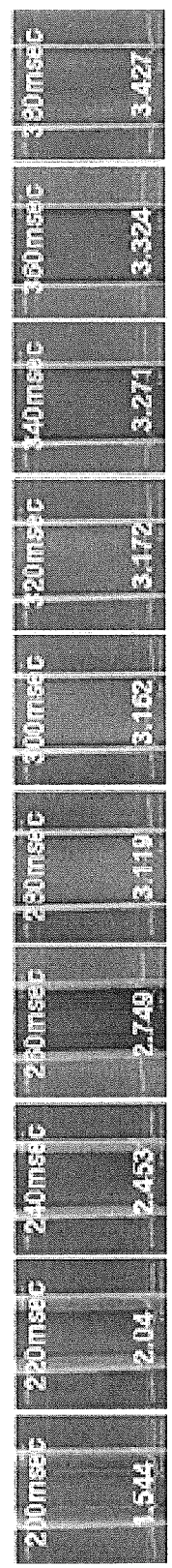

Patterns formed using a thermal type developed bottom anti-reflective coating (DBARC) and a photosensitive type DBARC according to the present invention are shown in FIGS. 15A and 15B. FIGS. 15A and 15B are SEM (Scanning Electron Microscope) photographs of patterns using a thermal type anti-reflective coating and a photosensitive type anti-reflective coating.

Numbers shown at upper portions of the respective photographs represent exposure energy (msec) supplied during formation of patterns and numbers shown at lower portions of the respective photographs represent trench sizes (um).

Referring to FIGS. 15A and 15B, when the thermal type DBARC was used, the exposure energy was increased up to 380 msec for exposure and developing. It was confirmed that the photoresist pattern was formed while not forming the DBARC pattern, and DBARC residues still remained on the lower substrate. By contrast, when the photosensitive type DBARC according to the present invention was used, it was confirmed that the pattern was formed while the photosensitive type DBARC was completely developed with an exposure energy of 380 msec without DBARC residues remaining on the lower substrate. In addition, it was also confirmed that the DBARC pattern was formed with a relatively low exposure energy of 200 msec.

That is to say, when the photosensitive type anti-reflective coating according to the embodiment of the present invention is used, a trench having a much better profile can be formed, compared to a case when the thermal type anti-reflective coating is used. Further, when the photosensitive type anti-reflective coating according to the embodiment of the present invention is used, an improved trench pattern can be formed, compared to a case when the thermal type anti-reflective coating is used.

EXPERIMENTAL EXAMPLE E

Figure 16A:
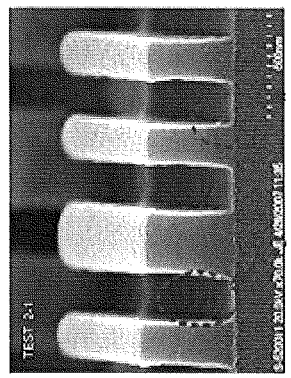
FIGS. 16A and 16B are vertical SEM photographs of patterns using a thermal type anti-reflective coating and a photosensitive type anti-reflective coating.
Figure 16B:
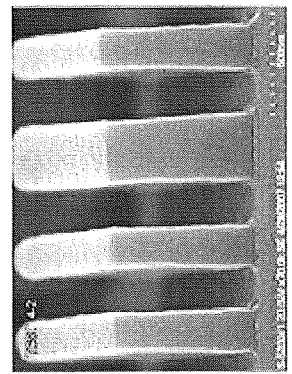

A pattern using the thermal type anti-reflective coating, and a photoresist pattern and an anti-reflective coating pattern formed using compositions for forming the photosensitive type DBARC are shown in FIGS. 16A and 16B, respectively. FIGS. 16A and 16B are vertical SEM photographs of patterns using a thermal type anti-reflective coating and a photosensitive type anti-reflective coating.

In FIG. 16A, the anti-reflective coating was formed to a thickness of 600 Å, and the photoresist film was formed to a thickness of 4000 Å. In FIG. 16B, the anti-reflective coating was formed to a thickness of 600 Å, and the photoresist film was formed to a thickness of 7000 Å.

Referring to FIG. 16A, when the thermal type anti-reflective coating is used, web and footing occurred to the patterns of the photoresist and the anti-reflective coating. By contrast, even if the thickness of the photoresist film shown in FIG. 16B is much greater than that of the photoresist film shown in FIG. 16A, the photoresist pattern and anti-reflective coating pattern having much clearer and sharper profiles were obtained. From this, the photosensitive type DBARC pattern formed using the composition for forming the photosensitive type DBARC was much more sensitive to i-line light, leading to a sufficiently activated acid generation While the present invention has been particularly shown and described with reference to exemplary embodiments thereof, it will be understood by those of ordinary skill in the art that various changes in form and details may be made therein without departing from the spirit and scope of the present invention as defined by the following claims. It is therefore desired that the present embodiments be considered in all respects as illustrative and not restrictive.

What is claimed is:

1. A photoresist composition for fabricating a probe array comprising:
   a photoacid generator having an onium salt comprising a sulfonium salt, which comprises a sulfonium salt cation portion represented by the formula (1) and a sulfonium salt anion portion represented by formula (2):

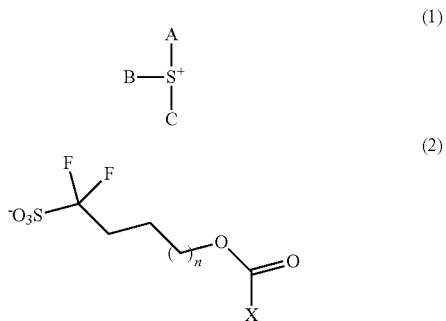

wherein in formula (1), each A, B, and C is one of a hydroxyl group, a cyclo group or a cycloalkyl group, and in the formula (2), n is an integer from 1 to 3, and X comprises a C3-C10 cycloalkyl group, an adamantyl group, or a cyclo heptane group comprising oxygen; and
an i-line reactive sensitizer including butyl benzyl phthalate.

2. The photoresist composition of claim 1, wherein the sulfonium salt is represented by formula (3):

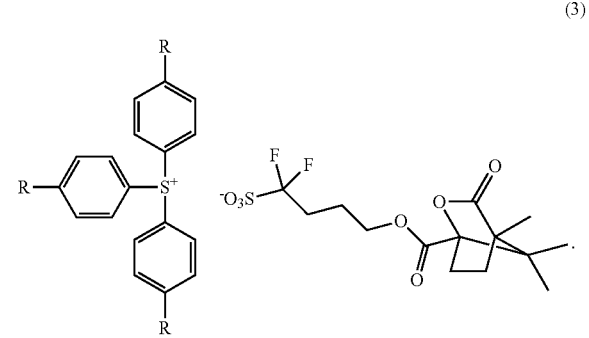

3. The photoresist composition of claim 1, wherein the sensitizer absorbs i-line light and activates an acid generating reaction by the photoacid generator.

4. The photoresist composition of claim 1, further comprising a resin, wherein the photoresist composition comprises 1 to 20 wt % of the resin, 1 to 10 wt % of the photoacid generator, 1 to 10 wt % of the sensitizer, and balance of a solvent.

5. The photoresist composition of claim 1, wherein the i-line light is light having a wavelength of 365 nm.

6. A composition for a photosensitive type developed bottom anti-reflective coating, the composition comprising:
a photoacid generator having an onium salt comprising a sulfonium salt, which comprises a sulfonium salt cation portion represented by formula (1) and a sulfonium salt anion portion represented by formula (2):

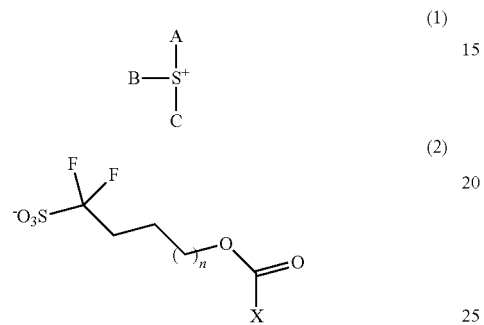

wherein in formula (1), each A, B, and C is one of a C1-C20 alkyl group, a C2-C20 alkoxy alkyl group, a C4-C20 aryl group, a C3-C20 cycloalkyl group, or a C5-C20 alkoxy cycloalkyl group, and in formula (2), n is an integer from 1 to 3, and X comprises a C4-C10 cyclo group, an alkyl group, a cycloalkyl group, an adamantyl group, or a cyclo heptane group comprising oxygen; and
an i-line reactive sensitizer including butyl benzyl phthalate.

7. The composition of claim 6, wherein the sulfonium salt is represented by formula (3):

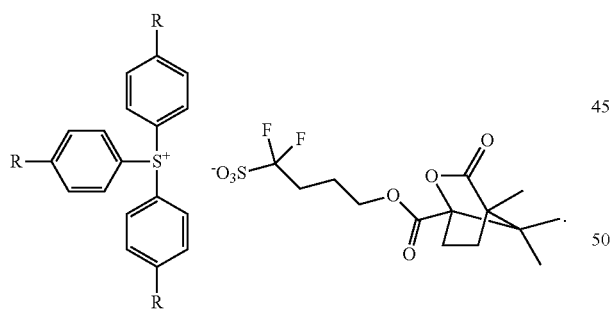

8. The composition of claim 6, wherein the sensitizer absorbs i-line light and activates an acid generating reaction by the photoacid generator.

9. The composition of claim 6, further comprising a polymer resin and a crosslinker, wherein the photoresist composition comprises 1 to 40 wt % of the polymer resin, 1 to 10 wt % of the photoacid generator, 1 to 10 wt % of the sensitizer, 5 to 20 wt % of the crosslinker, and balance of a solvent.

10. The composition of claim 6, wherein the i-line light is light having a wavelength of 365 nm.

11. A photoresist composition for fabricating a probe array comprising:
a photoacid generator having an onium salt comprising a sulfonium salt, which comprises a sulfonium salt cation portion represented by the formula (1) and a sulfonium salt anion portion represented by formula (2):

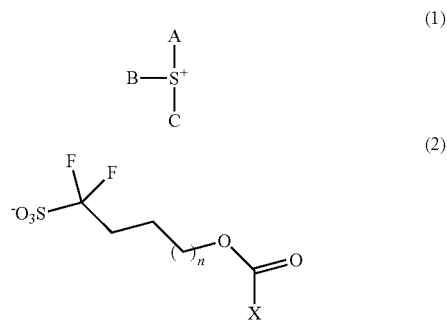

wherein in formula (1), each A, B, and C is one of a hydroxyl group, a cyclo group or a cycloalkyl group, and in the formula (2), n is an integer from 1 to 3, and X comprises a C3-C10 cycloalkyl group, an adamantyl group, or a cyclo heptane group comprising oxygen; and
an i-line reactive sensitizer comprising at least one of the following compounds:

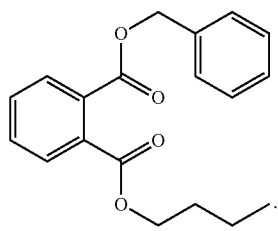 [SMILES: CCCCOC(=O)c1ccccc1C(=O)OCc1ccccc1]

12. The photoresist composition of claim 11, further comprising 1-20 wt % of a polymer resin comprising methacrylate, 1 to 10 wt % of the photoacid generator, 1 to 10 wt % of the sensitizer, and balance of a solvent.

13. The photoresist composition of claim 1, further comprising 1-20 wt % of a polymer resin comprising methacrylate, 1 to 10 wt % of the photoacid generator, 1 to 10 wt % of the sensitizer, and balance of a solvent.

* * * * *